United States Patent [19]

Irikura et al.

[11] 4,448,962

[45] May 15, 1984

[54] SUBSTITUTED QUINOLINE CARBOXYLIC ACID DERIVATIVES

[75] Inventors: Tsutomu Irikura, Tokyo; Seigo Suzue, Saitama; Akira Ito, Saitama; Hiroshi Koga, Saitama, all of Japan

[73] Assignee: Kyorin Seiyaku Kabushiki Kaisha, Tokyo, Japan

[21] Appl. No.: 311,343

[22] Filed: Oct. 14, 1981

Related U.S. Application Data

[63] Continuation-in-part of Ser. No. 80,519, Oct. 1, 1979, abandoned.

[30] Foreign Application Priority Data

Sep. 29, 1978 [JP]   Japan .................................. 53-120216

[51] Int. Cl.³ .................. C07D 401/02; A61K 31/495
[52] U.S. Cl. .................................... 544/362; 424/250; 544/358; 544/363; 544/384; 544/386; 544/399; 544/402; 544/403; 546/123; 546/156
[58] Field of Search ................. 544/362, 363; 424/250

[56] References Cited

U.S. PATENT DOCUMENTS

| | | | |
|---|---|---|---|
| 3,149,104 | 9/1964 | Lesher et al. | 544/362 |
| 3,590,036 | 6/1971 | Lesher et al. | 544/362 |
| 3,849,421 | 11/1974 | Nakagome et al. | 544/362 |
| 4,017,622 | 4/1977 | Minami et al. | 544/363 |
| 4,146,719 | 3/1979 | Irikura | 544/363 |
| 4,292,315 | 9/1981 | Pesson | 424/250 |
| 4,352,808 | 10/1982 | Matsumoto et al. | 544/362 |
| 4,359,578 | 11/1982 | Matsumoto et al. | 544/363 |

OTHER PUBLICATIONS

Tsutomu, "Chemical Abstracts", vol. 89, 1978, Col. 129,537x.
Japan Kokai, Tokkyo Kobo, 79-14,978, "Chemical Abstracts", vol. 90, 1979, col. 163334j.

*Primary Examiner*—Donald G. Daus
*Assistant Examiner*—James H. Turnipseed
*Attorney, Agent, or Firm*—Toren, McGeady and Stanger

[57] ABSTRACT

This invention relates to new compounds of value as antibacterial agents. More particularly, it relates to quinoline carboxylic acid derivatives, the hydrates and the acid or alkali addition salts thereof.

3 Claims, No Drawings

SUBSTITUTED QUINOLINE CARBOXYLIC ACID DERIVATIVES

CROSS-REFERENCE TO RELATED APPLICATIONS

This is a continuation-in-part of copending application Ser. No. 080,519, filed Oct. 1, 1979, now abandoned.

BACKGROUND OF THE INVENTION

1. Field of the Invention

This invention relates to quinoline carboxylic acid derivatives for use as antibacterial agents.

2. Description of the Prior Art

Antibacterial agents, such as, nalidixic acid, have been proved highly effective in the therapy of infections due to gram-negative bacteria. However, such agents suffer from the serious drawback of being ineffective against numerous strains of bacteria, e.g., most gram-positive bacteria and pseudomonas aeruginosa. Infections from these strains have progressively increased for the last two decades and have exhibited resistance to chemotherapy.

SUMMARY OF THE INVENTION

We have discovered a new series of compounds which are particularly useful in that they possess potent antibacterial activity against both gram-positive and gram-negative bacteria, including pseudomonas aeruginosa.

The new compounds of the present invention are quinoline carboxylic acid derivatives, the hydrates and the acid or alkali addition salts thereof.

More particularly, compounds in accordance with the present invention have the formula

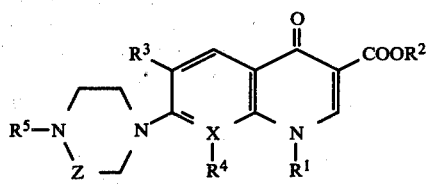

wherein
$R^1$ represents lower alkyl, lower alkenyl, halogenated lower alkyl, or aryl-substituted lower alkyl group;
$R^2$ is hydrogen or ethyl,
$R^3$ represents halogen atom, hydrogen
X represents carbon or nitrogen atom,
$R^4$ represents fluorine or hydrogen when X is carbon and nothing when X is nitrogen atom,
$R^5$ represents hydrogen, lower alkyl, or acetyl, carboxymethyl, ethoxycarbonylmethyl, trifluoroacetyl, benzyl, p-aminobenzyl, p-nitrobenzyl, phthalidyl, or nitroso group,
Z represents —CH$_2$— or —CO— group.

Further, compounds of the present invention include the hydrates and pharmaceutically acceptable acid addition salts of the foregoing.

The products of the present invention are prepared by heating piperazine derivatives with 1-substituted-6,7-dihalogeno-4-oxo-1,4-dihydroquinoline-3-carboxylic acid derivatives in a non-reactive solvent, such as, for example, water, alcohol, pyridine, picoline, dimethylformamide, dimethylsulfoxide, or the like or in the absence of a solvent and/or by hydrolysis with aqueous hydrochloric acid or aqueous alkali.

DESCRIPTION OF THE PREFERRED EMBODIMENTS

More particularly, the present invention relates to the compounds and their physiologically non-toxic salts of the general formula (I)

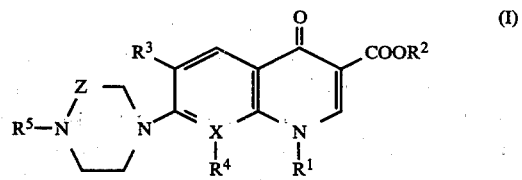

wherein
X represents carbon or nitrogen atom, provided that $R^4$ has no radical when X is nitrogen;
Z represents CO or CH$_2$;
$R^1$ is a member selected from the group consisting of methyl, ethyl, propyl, benzyl, 2-hydroxyethyl, allyl, vinyl or 2-fluoroethyl;
$R^2$ represents hydrogen or ethyl group;
$R^3$ is a member selected from the group consisting of hydrogen, chlorine, bromine or fluorine;
$R^4$ represents hydrogen or fluorine,
$R^5$ is a radical selected from the group consisting of hydrogen, methyl, ethyl, benzyl, ethoxycarbonylmethyl, carboxymethyl, acetyl, trifluoroacetyl, phthalidyl, nitroso, p-nitrobenzyl or p-aminobenzyl; provided that $R^3$ and $R^4$ have not a hydrogen atom simultaneously; $R^5$ has no hydrogen when $R^1$ is ethyl, X is carbon, $R^3$ is fluorine or chlorine, Z is CH$_2$, and $R^2$ and $R^4$ are hydrogen; $R^5$ has no hydrogen when $R^1$ is ethyl, X is carbon, $R^2$ and $R^3$ are hydrogen, Z is CH$_2$ and $R^4$ is chlorine; $R^2$ has no hydrogen when $R^1$ is ethyl, X is carbon, $R^4$ is hydrogen, $R^3$ is fluorine, Z is CH$_2$ and $R^5$ is methyl.

The physiologically non-toxic salts of said general formula (I) are, for example, metallic salts, such as, of sodium, potassium and calcium, organic base salts, such as, of ethanol amine and diethanolamine, inorganic salts, such as, of hydrochloric acid, sulfuric acid and phosphoric acid, and organic acid salts, such as, of acetic acid, methanesulfonic acid, succinic acid and lactic acid.

The compounds of the present invention having general formula (I) are particularly useful as an antibacterial agent in that they possess potent antibacterial activity against both gram-positive and gram-negative bacteria, including Pseudomonas Aeruginosa.

The compounds of general formula (I) are prepared by the reaction of a compound of the general formula (II)

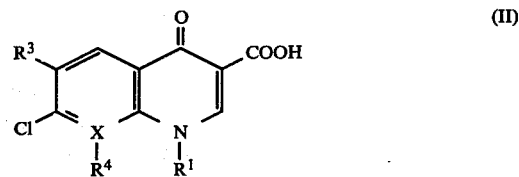

wherein X, $R^1$, $R^3$ and $R^4$ have the same meaning as above, with a piperazine derivative of the general formula (III),

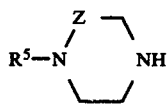

wherein $R^5$ and Z have the same meaning as above, in the absence of a solvent or in the presence of a non-reactive solvent such as water and alcohols, a non-reactive organic base, such as, pyridine, picoline, lutidine, collidine and triethylamine; an aprotic polar solvent, such as, N,N-dimethylformamide and dimethylsulfoxide; and an ether, such as, monoglyme, diglyme and triglyme, at a temperature from room temperature to 200° C., preferably at 100°-180° C.; or are prepared by the reaction of a compound of the general formula (IV),

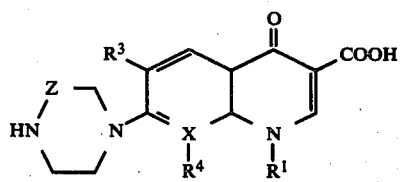

wherein X, Z, $R^1$, $R^3$ and $R^4$ have the same meaning as above, with a compound of the general formula (V),

  (V)

wherein $R^5$ is defined as above and $\gamma$ represents chlorine, bromine, iodine, acetoxy group, trifluoroacetoxy group, hydroxy or sulfonyloxy group, in the presence or absence of a base, such as, triethylamine, pyridine, alkali carbonate and alkali hydroxide, in an aprotic polar solvent, such as, N,N-dimethylformamide and dimethylsulfoxide, or in a non-reactive solvent, such as, water, alcohols, ethers, dichloromethane, chloroform and other halogenated hydrocarbon; or are prepared by the reaction of a compound of the general formula (IV) with an aqueous solution of a nitrous salt, such as, sodium nitrite in the presence of an acid, such as, hydrochloric acid and acetic acid; or are prepared by the reaction of a compound of the general formula (VI)

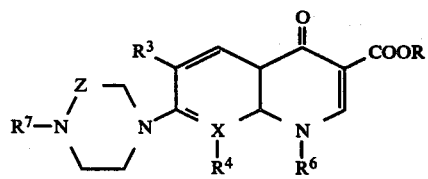

wherein X, Z, $R^2$, $R^3$ and $R^4$ have the same meaning as above, $R^6$ represents ethyl or 2-chloroethyl group and $R^7$ represents acetyl, ethoxycarbonylmethyl or hydrogen; with an alkaline solution, such as, of sodium hydroxide and potassium hydroxide; or are prepared further by the reaction of a compound of the general formula (VII),

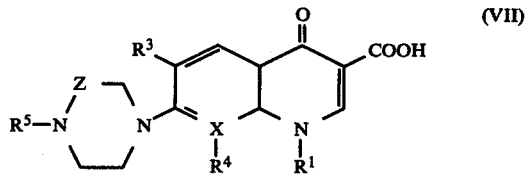

wherein X, Z, $R^1$, $R^3$, $R^4$ and $R^5$ have the same meaning as above, with ethanol in the presence of an inorganic or organic acid, such as, hydrochloric acid, sulfuric acid and p-toluenesulfonic acid, or in the presence of a reagent, such as, thionyl chloride; or are prepared also by the reduction of a compound of the general formula (VIII)

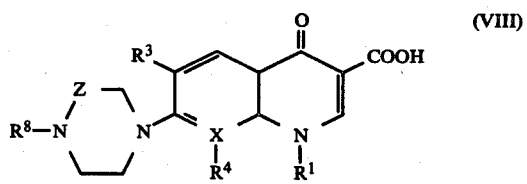

wherein X, Z, $R^1$, $R^2$ and $R^4$ have the same meaning as above and $R^8$ represents p-nitrobenzyl group, with zinc and acetic acid or by the catalytic reduction thereof with hydrogen in the presence of palladium-carbon or Raney-Nickel.

The following examples illustrate the present invention.

EXAMPLE 1

To a mixture of 6-amino-7-chloro-1-ethyl-1,8-naphthyridine-3-carboxylic acid ethyl ester (4.0 g), concentrated hydrochloric acid (3.4 ml) and water (4 ml) was added dropwise, a solution of sodium nitrate (1.0 g) in water (3 ml) with stirring at 0° C., the reaction mixture was stirred vigorously at the same temperature for 30 minutes. A solution of sodium fluoborate (2.2 g) in water (5 ml) was added to the reaction mixture, the reaction mixture was stirred at 0°-5° C. for 1 hour. After filtering, the solid was washed with 5% cold solution of sodium fluoborate, cold methanol and diethyl ether, then dried to give 7-chloro-3-ethoxycarbonyl-1-ethyl-1,4-dihydro-4-oxo-6-(1,8-naphthyridine)-diazonium tetrafluoroborate.

The above salt was heated at about 170° C., alkalized with aqueous sodium bicarbonate solution and extracted with chloroform. The chloroform layer was washed with water, dried over anhydrous sodium sulfate, and chloroform was evaporated to give 7-chloro-1-ethyl-6-fluoro-1,4-dihydro-4-oxo-1,8-naphthyridine-3-carboxylic acid ethyl ester.

Melting point: 150°-160° C.

A mixture of piperazine (0.86 g), the above ester (1.0 g) and ethanol (20 ml) was refluxed for 2.5 hrs. The solvent was evaporated, and the residue was extracted with chloroform. The chloroform layer was washed with water, dried over anhydrous sodium sulfate, and chloroform was evaporated. The residue was purified by chromatography to give 1-ethyl-6-fluoro-1,4-dihydro-4-oxo-7-(1-piperazinyl)-1,8-naphthyridine-3-carboxylic acid ethyl ester.

A mixture of the 1-ethyl-1,4-dihydro-6-fluoro-7-(1-piperazinyl)-4-oxo-1,8-naphthylidine-3-carboxylic acid ethyl ester (0.17 g), sodium hydroxide (0.06 g) and water (0.5 ml) was heated with stirring at 80°–90° C. for 40 minutes. The reaction mixture was evaporated under vacuum and the residue was recrystallized from a mixture of concentrated hydrochloric acid and ethanol to give 0.08 g of 1-ethyl-1,4-dihydro-6-fluoro-7-(1-piperazinyl)-4-oxo-1,8-naphthyridine-3-carboxylic acid hydrochloride. Melting point: >300° C.

IR$\nu_{max}^{KBr}$ cm$^{-1}$: 1720(COOH), 1628(CO).

MS m/e: 320 (M+—HCl), 276(M+—HCl—$CO_2$).

EXAMPLE 2

A mixture of 1-ethyl-6-fluoro-7-(1-piperazinyl)-4-oxo-1,4-dihydro-quinoline-3-carboxylic acid (0.96 g) (3 millimole), iodoethyl (0.94 g) (6 millimole), triethylamine (0.6 g) (6 millimole) and 10 ml DMF was heated to 70° to 80° C. for 2.5 hours under stirring. After cooling, the reaction mixture was evaporated under vacuum and the residue was dissolved in dichloromethane, washed with water, dried over anhydrous $Na_2SO_4$ and the solvent was removed. The residue was recrystallized from a mixture of $CHCl_3$ and benzene to obtain 0.75 g (72%) of 1-ethyl-6-fluoro-7-(4-ethyl-1-piperazinyl)-4-oxo-1,4-dihydroquinoline-3-carboxylic acid.

Melting point: 251°–253° C.

| Analysis ($C_{18}H_{22}O_3N_3F$·½ $H_2O$) | | | |
|---|---|---|---|
| | C | H | N |
| Calculated (%) | 61.44 | 6.45 | 11.94 |
| Measured (%) | 61.49 | 6.24 | 11.70 |

EXAMPLE 3

Thionyl chloride (2.4 g) was added dropwise to a solution of 1-(2-hydroxyethyl)-6-fluoro-7-(4-acetyl-1-piperazinyl)-4-oxo-1,4-dihydroquinoline-3-carboxylic acid (0.38 g) in ethanol (20 ml) under cooling with an ice-water bath, and the reaction mixture was refluxed for 5.5 hrs. The reaction mixture was evaporated to dryness, the residue was neutralized with aqueous potassium carbonate solution, and the solution was extracted with chloroform. After removing the chloroform, the residue was recrystallized from a mixture of methylene chloride and ethyl acetate to give 0.36 g of 1-(2-hydroxyethyl)-6-fluoro-7-(4-acetyl-1-piperazinyl)-4-oxo-1,4-dihydroquinoline-3-carboxylic acid ethyl ester.

Melting point: 221°–223° C. (decomposed).

A solution of thionyl chloride (1.19 g) in chloroform (5 ml) was added dropwise to a mixture of the above ester (0.405 g) and pyridine (0.095 g) in chloroform (10 ml) under cooling with an ice-water bath and the reaction mixture was allowed to stand overnight at room temperature. After the reaction mixture was concentrated, the residue was neutralized with aqueous potassium carbonate solution, and extracted with chloroform. The chloroform layer was washed with water, dried over anhydrous sodium sulfate.

After chloroform was evaporated, the residue was recrystallized from ethanol to give 0.36 g (86%) of 1-(2-chloroethyl)-6-fluoro-7-(4-acetyl-1-piperazinyl)-4-oxo-1,4-dihydroquinoline-3-carboxylic acid ethyl ester.

Melting point: 218°–219° C.

A mixture of the 1-(2-chloroethyl)-6-fluoro-7-(4-acetyl-1-piperazinyl)-4-oxo-1,4-dihydro-quinoline-3-carboxylic acid ethyl ester (65 mg) (0.153 millimole), NaOH (0.10 g), $H_2O$ (1 ml), and ethanol (1 ml) was heated at 95°–100° C. for 4 hours under stirring. After cooling, the reaction mixture was acidified with hydrochloric acid, and evaporated under vacuum. The residue was recrystallized from a mixture of water and ethanol to obtain 48 mg of 1-vinyl-6-fluoro-7-(1-piperazinyl)-4-oxo-1,4-dihydro-quinoline-3-carboxylic acid hydrochloride.

Melting point: 280°–283° C. (decomposed).

IR$\nu_{max}^{KBr}$ cm$^{-1}$: 1720 (COOH), 1625 (CO).

MS m/e: 317 (M+—Cl), 273 M+—HCl—$CO_2$).

EXAMPLE 4

A mixture of 1-vinyl-6-fluoro-7-chloro-4-oxo-1,4-dihydroxyquinoline-3-carboxylic acid (0.89 g) (3.3 millimole) N-methylpiperazine (1.7 g) (17 millimole) and 2 ml pyridine was heated at 135°–145° C. for 12 hours. After cooling, the reaction mixture was evaporated under vacuum, acidified with acetic acid, and undissolved matter removed by filtration. The filtrate was neutralized with an aqueous solution of caustic soda, extracted with $CHCl_3$, washed with water, dried over anhydrous $Na_2SO_4$, and the solvent was removed. The residue was dissolved in aqueous HCl and ethanol was added. The solution was ice cooled. The precipitate was filtered, washed with ethanol, and dried to obtain a slightly yellow powder of 0.05 g of 1-vinyl-6-fluoro-7-(4-methyl-1-piperazinyl)-4-oxo-1,4-dihydroquinoline-3-carboxylic acid hydrochloride. Melting point: not lower than 300° C.

IR$\nu_{max}^{KBr}$ cm$^{-1}$: 1720 (COOH), 1630 (CO).

MS m/e: 331 (M+—HCl), 287(M+—HCl—$CO_2$).

EXAMPLE 5

A mixture of 3-chloro-4-fluoroaniline (1.46 g) and diethyl ethoxymethylene malonate (2.16 g) was heated at 120°–130° C. After 2 hours, the resulting ethanol was evaporated off. The residue was added to diphenyl ether (50 ml) and refluxed for 1 hour. After the solution cooled, the resulting precipitate was filtered, washed with benzene, and dried. The solid was recrystallized from N,N-dimethylformamide (DMF) to give 7-chloro-6-fluoro-1,4-dihydro-4-oxoquinoline-3-carboxylic acid ethyl ester (3.2 g).

Melting point: above 300° C.

To a stirred mixture of the above ester (1.35 g), potassium carbonate (1.73 g) and DMF (20 ml), 4.35 g of 2-fluoroethyl iodide was added and the mixture was stirred at 80°–90° C. for 9.5 hours. After the solvent evaporated off, the residue was extracted with dichromomethane, the dichloromethane layer was washed with water, and dried. The solvent was evaporated. The residue was added to 18% hydrochloric acid (20 ml) and refluxed for 3 hours. After the mixture cooled, the solid was filtered, washed with water, dried, and recrystallized from a mixture of DMF and ethanol to give 7-chloro-6-fluoro-1-(2-fluoroethyl)-1,4-dihydro-4-oxoquinoline-3-carboxylic acid (1.0 g).

Melting point: 262°–264° C.

A mixture of 1-(2-fluoroethyl)-6-fluoro-7-chloro-4-oxo-1,4-dihydroquinoline-3-carboxylic acid (0.87 g) (3 millimole), piperazine (1.3 g) (15 millimole) and pyridine (4 ml) piperazine was heated at 135° to 145° C. for 12 hours. After cooling, the reaction mixture was evaporated under vacuum, the residue was acidified with acetic acid, the undissolved matter was filtered off. The filtrate was neutralized in an aqueous solution of caustic soda. The precipitate was filtered, washed, dried and dissolved in diluted HCl. Ethanol was added and the solution was ice cooled. The precipitate was filtered, washed with ethanol and dried and recrystallized from ethanol to obtain 0.30 g (27%) of 1-(2-fluoroethyl)-6-fluoro-7-(1-piperazinyl)-4-oxo-1,4-dihydroquinoline-3-carboxylic acid hydrochloride in powder form.

Melting point: 292° C. (decomposition).

Analysis: $C_{16}H_{17}O_3N_3F_2 \cdot HCl \cdot H_2O$

|  | C | H | N |
| --- | --- | --- | --- |
| Calculated (%) | 49.05 | 5.15 | 10.72 |
| Measured (%) | 48.91 | 4.97 | 10.68 |

EXAMPLE 6

A mixture of 1-(2-fluoroethyl)-6-fluoro-7-chloro-4-oxo-1,4-dihydroquinoline-3-carboxylic acid (0.72 g) (2.5 millimole), N-methylpiperazine (1.25 g) (12.5 millimole) and 2 ml pyridine was heated at 135°–145° C. for 10 hours. After cooling, the mixture was evaporated under vacuum. The residue was acidified with acetic acid. The undissolved matter was filtered off. The filtrate was neutralized with an aqueous solution of caustic soda. The presipitate was filtered, washed and dried and recrystallized from a mixture of DMF and ethanol. 0.50 g (57%) of 1-(2-fluoroethyl)-6-fluoro-7-(4-methyl-1-piperazinyl)-4-oxo-1,4-dihydroquinoline-3-carboxylic acid was obtained.

Melting point: 256°–258° C.

Analysis: $C_{17}H_{19}O_3N_3F_2$

|  | C | H | N |
| --- | --- | --- | --- |
| Calculated (%) | 58.11 | 5.45 | 11.96 |
| Measured (%) | 58.13 | 5.47 | 11.95 |

EXAMPLE 7

A mixture of 1-ethyl-1,4-dihydro-6-fluoro-7-[4-(p-nitrobenzyl)-1-piperazinyl]-4-oxoquinoline-3-carboxylic acid (2.0 g), 5% Pd/C (0.40 g) and 50 ml glacial acetic acid was made to absorb a theoretical amount of hydrogen (296 ml). The catalyst was removed and the filtrate was evaporated under vacuum. The residue was recrystallized from concentrated HCl and ethanol to obtain 1.4 g (64%) of 1-ethyl-7-[(4-p-aminobenzyl)-1-piperazinyl]-1,4-dihydro-6-fluoro-4-oxo-quinoline-3-carboxylic acid hydrochloride. Melting point: 220°–223° C. (decomposition).

Analysis: $C_{23}H_{25}O_3N_4F \cdot 2HCl \cdot \frac{1}{2} H_2O$

|  | C | H | N |
| --- | --- | --- | --- |
| Calculated (%) | 54.55 | 5.57 | 11.06 |
| Measured (%) | 54.72 | 5.47 | 10.98 |

EXAMPLE 8

A mixture of 1-ethyl-7-chloro-1,4-dihydro-6-fluoro-4-oxoquinoline-3-carboxylic acid (0.80 g), 2-oxopiperazine (3.0 g) and 4 ml pyridine was heated for 18 hours. The reaction mixture was evaporated under vacuum, an aqueous solution of caustic soda was added to adjust the pH to 10, ice cooled and the undissolved matter was collected and washed with a small amount of an aqueous solution of NaOH. The filtered product was suspended in water, acidified with acetic acid, filtered and washed. The product obtained was dissolved in an aqueous solution of NaOH and acidified with acetic acid. The precipitate was filtered, washed and dried to obtain 0.32 g (32%) of 1-ethyl-1,4-dihydro-6-fluoro-7-(3-oxo-1-piperazinyl)-4-oxoquinoline-3-carboxylic acid.

Melting point: not lower than 300° C.

Analysis: $C_{16}H_{16}O_4N_3F \cdot \frac{1}{2} H_2O$

|  | C | H | N |
| --- | --- | --- | --- |
| Calculated (%) | 56.14 | 5.01 | 12.27 |
| Measured (%) | 56.32 | 4.79 | 12.27 |

EXAMPLE 9

A mixture of 1-ethyl-6,7-dichloro-4-oxo-1,4-dihydroquinoline-3-carboxylic acid 2.86 g (0.01 mole), N-methylpiperazine 10 g (0.1 mole) and 15 ml water was heated in a sealed tube at 125°–130° C. (inner temperature) for 19 hours. After cooling, the reaction mixture was evaporated under vacuum and acidified with acetic acid. Insoluble matters were filtered off and the filtrate was neutralized with an aqueous solutiong of NaOH to pH 7, extracted with $CHCl_3$, dried with anhydrous $Na_2SO_4$, and the solvent was distilled off. The residue was recrystallized from a mixed solvent of $CHCl_3$ and benzene to give 1.05 g (30%) of 1-ethyl-6-chloro-7-(4-methyl-1-piperazinyl)-4-oxo-1,4-dihydro-quinoline-3-carboxylic acid. Colorless needles.

Melting point: 257°–260° C.

Analysis: $C_{17}H_{20}O_3N_3Cl$

|  | C | H | N |
| --- | --- | --- | --- |
| Calculated (%) | 58.37 | 5.76 | 12.01 |
| Measured (%) | 58.05 | 5.66 | 11.87 |

EXAMPLE 10

A mixture of 1-ethyl-6-chloro-7-(1-piperazinyl)-4-oxo-1,4-dihydroquinoline-3-carboxylic acid 1.7 g (0.005 mole), iodoethyl 1.6 g (0.01 mole), triethylamine 1.0 g (0.01 mole) and dimethylformamide (hereinafter DMF) 20 ml was heated at 90°–100° C. for 7 hours under stirring. After cooling, the reaction mixture was evaporated under vacuum. The residue was dissolved in $CHCl_3$, washed with water, dried with anhydrous $Na_2SO_4$, and the solvent was distilled off. The residue was recrystallized from a mixed solvent of DMF and ethanol to obtain 0.4 g (22%) of 1-ethyl-6-chloro-7-(4-ethyl-1-piperazinyl)-4-oxo-1,4-dihydroquinoline-3-carboxylic acid. Colorless needles.

Melting point: 245°–248° C.

Analysis: $C_{18}H_{22}O_3N_3Cl$

|  | C | H | N |
| --- | --- | --- | --- |
| Calculated (%) | 59.42 | 6.09 | 11.55 |
| Measured (%) | 59.21 | 6.10 | 11.57 |

EXAMPLE 11

A mixture of 1-ethyl-6-chloro-7-(1-piperazinyl)-4-oxo-1,4-dihydroquinoline-3-carboxylic acid 1.7 g (0.005 mole), benzylchloride 1.26 g (0.01 mole), triethylamine (0.01 mole) and DMF 10 ml was heated at 90°–100° C. for 7 hours under stirring. After cooling, the reaction mixture was dried up under vacuum. The residue was dissolved in $CHCl_3$, washed with water, dried with anhydrous $Na_2SO_4$, and the solvent was distilled off.

The residue was recrystallized from a mixed solvent of DMF and ethanol to obtain 1.1 g (52%) of 1-ethyl-6-chloro-7-(4-benzyl-1-piperazinyl)-4-oxo-1,4-dihydroquinoline-3-carboxylic acid. Colorless prism.

Melting point: 232° C.

Analysis: $C_{23}H_{24}O_3N_3Cl$.

EXAMPLE 12

A mixture of 1-ethyl-6-chloro-7-(1-piperazinyl)-4-oxo-1,4-dihydroquinoline-3-carboxylic acid 1.7 g (0.005 mole), anhydrous trifluoroacetic acid 4.2 g (0.02 mole) and dichloromethane 4 ml was stirred at room temperature for 3 hours. The reaction mixture was evaporated under vacuum and the residue was recrystallized from a mixed solvent of DMF and ethanol to obtain 1.8 g (86%) of 1-ethyl-6-chloro-7-(4-trifluoroacetyl-1-piperazinyl)-4-oxo-1,4-dihydroquinoline-3-carboxylic acid. Colorless plates. Melting point: 297°–298° C. (decomposition).

| Analysis: $C_{18}H_{17}N_3O_4ClF_3$ | | | |
|---|---|---|---|
| | C | H | N |
| Calculated (%) | 50.07 | 3.97 | 9.73 |
| Measured (%) | 50.01 | 3.95 | 9.51 |

EXAMPLE 13

A mixture of 1-ethyl-6-chloro-7-(1-piperazinyl)-4-oxo-1,4-dihydroquinoline-3-carboxylic acid 1.7 g (0.01 mole), ethylchloroacetate 1.2 g (0.01 mole), triethylamine 1.0 g (0.01 mole) and DMF 10 ml was heated at 90°–100° C. for 3 hours under stirring. The reaction mixture was cooled, evaporated under vacuum, the residue was dissolved in dichloromethane, washed with water, dried with anhydrous $Na_2SO_4$, and the solvent was distilled off. The residue was recrystallized from a mixed solvent of DMF and ethanol to obtain 2.1 g (quantitative) of 1-ethyl-6-chloro-7-(4-ethoxycarbonylmethyl-1-piperazinyl)-4-oxo-1,4-dihydroquinoline-3-carboxylic acid. Colorless powders.

Melting point: 230°–232° C.

| Analysis: $C_{20}H_{24}N_3O_5Cl$ | | | |
|---|---|---|---|
| | C | H | N |
| Calculated (%) | 56.94 | 5.73 | 9.96 |
| Measured (%) | 57.05 | 5.78 | 9.95 |

EXAMPLE 14

A mixture of 1-ethyl-6-chloro-7-(4-ethoxycarbonylmethyl-1-piperazinyl)-4-oxo-1,4-dihydroquinoline-3-carboxylic acid 0.85 g (0.002 mole), NaOH 0.4 g (0.01 mole), $H_2O$ 5 ml and ethanol 5 ml was refluxed for 3 hours by heating. After cooling, the reaction mixture was acidified with acetic acid. The precipitated crystals are collected by filtration, washed successively with water and ethanol, and dried. Recrystallizing the residue with the use of a mixed solvent of DMF and ethanol, 0.8 g (quantitative) of 1-ethyl-6-chloro-7-(4-carboxymethyl-1-piperazinyl)-4-oxo-1,4-dihydroquinoline-3-carboxylic acid was obtained. Colorless powders.

Melting point: 262°–264° C. (decomposition)

| Analysis: $C_{18}H_{20}N_3O_5Cl.\frac{1}{2} H_2O$ | | | |
|---|---|---|---|
| | C | H | N |
| Calculated (%) | 53.67 | 5.25 | 10.42 |
| Measured (%) | 53.76 | 5.06 | 10.29 |

EXAMPLE 15

A mixture of 1-ethyl-6-chloro-7-(1-piperazinyl)-4-oxo-1,4-dihydroquinoline-3-carboxylic acid hydrochloride 1.9 g (0.005 mole), 3-hydroxyphthalide 0.75 g (0.005 mole), triethylamine 0.5 g (0.005 mole) and DMF 10 ml was heated at 100°–110° C. for 8 hours under stirring. After cooling, the reaction mixture was evaporated under vacuum. The residue was dissolved in dichloromethane, washed with water and dried with anhydrous $Na_2SO_4$. After removing the solvent, the residue was recrystallized from a mixed solvent of DMF and ethanol to obtain 1.8 g (78%) of 1-ethyl-6-chloro-7-(4-phthalidyl-1-piperazinyl)-4-oxo-1,4-dihydroquinoline-3-carboxylic acid. Colorless powders.

Melting point: 279°–280° C. (decomposition).

| Analysis: $C_{24}H_{22}N_3O_5Cl$ | | | |
|---|---|---|---|
| | C | H | N |
| Calculated (%) | 61.61 | 4.74 | 8.98 |
| Measured (%) | 61.50 | 4.69 | 8.96 |

EXAMPLE 16

A mixture of 1-ethyl-7-chloro-8-fluoro-4-oxo-1,4-dihydroquinoline-3-carboxylic acid 2.7 g (0.01 mole) and piperazine hexahydrate 19.4 g (0.1 mole) was heated in a sealed tube at 130°–140° C. (inner temperature) for 16 hours. After cooling, the reaction mixture was dried up under vacuum, and the residue was acidified with hydrochloric acid. The precipitated crystals are collected by filtration, washed successively with water and ethanol, and dried. Recrystallizing the precipitate from a mixed solvent of water and ethanol, 2.9 g (82%) of 1-ethyl-7-(1-piperazinyl)-8-fluoro-4-oxo-1,4-dihydroquinoline-3-carboxylic acid hydrochloric was obtained. Colorless needles.

Melting point: not lower than 300° C.

| Analysis: $C_{16}H_{18}O_3N_3F.\frac{1}{2} H_2O$ | | | |
|---|---|---|---|
| | C | H | N |
| Calculated (%) | 52.68 | 5.52 | 11.52 |
| Measured (%) | 52.55 | 5.32 | 11.45 |

EXAMPLE 17

A mixture of 1-ethyl-6-fluoro-7-chloro-1,4-dihydro-4-oxoquinoline-3-carboxylic acid (1.9 g), piperazine hexahydrate (15 g) and water (15 ml) was heated at 170° C. in a sealed tube for 16 hours. After evaporation of the solvent, the residue was acidified with diluted hydrochloric acid, heated at 100° C., and the hot solution was filtered. The filtrate was evaporated to dryness. The residue was dissolved in 10% sodium hydroxide and neutralized with acetic acid. The precipitate was collected, washed with water, dried, and recrystallized from ethanol to give 1-ethyl-6-fluoro-1,4-dihydro-7-(1-piperazinyl)-4-oxoquinoline-3-carboxylic acid as colorless powder.

Melting point: 226°–227° C.

The above acid was dissolved in ethanol and acidified with concentrated hydrochloric acid. The resulting precipitate was collected, washed with ethanol, and dried to give 1-ethyl-6-fluoro-1,4-dihydro-7-(1-piperazinyl)-4-oxoquinoline-3-carboxylic acid hydrochloride as colorless needles.

Melting point: above 300° C. The ethyl ester was prepared.

3.4 g of $SOCl_2$ was dropped slowly into a mixture of 1-ethyl-6-fluoro-7-(1-piperazinyl-4-oxo-1,4-dihydroquinoline-3-carboxylic acid hydrochloride 0.5 g and anhydrous ethanol 20 ml by cooling with an ice-water bath. After the addition completed, the reaction mixture was refluxed for 5.5 hours by heating. After cooling, the reaction mixture was dried up under vacuum. The residue was made basic with an aqueous solution of $K_2CO_3$, extracted with dichloromethane, washed with water, dried over anhydrous $Na_2SO_4$, and the solvent was evaporated off. Recrystallizing the residue from a mixed solution of benzene and hexane, 0.5 g (quantitative) of 1-ethyl-6-fluoro-7-(1-piperazinyl)-4-oxo-1,4-dihydroquinoline-3-carboxylic acid ethyl ester was obtained.

Melting point: 182°–184° C.

Analysis: $C_{18}H_{22}O_3N_3F$

|  | C | H | N |
|---|---|---|---|
| Calculated (%) | 62.23 | 6.38 | 12.10 |
| Measured (%) | 62.02 | 6.34 | 11.97 |

EXAMPLE 18

The starting material for this example was synthesized by the same method as in Example 5, using methyl iodide instead of 2-fluoroethyl iodide.

A mixture of 1-methyl-6-fluoro-7-chloro-4-oxo-1,4-dihydroquinoline-3-carboxylic acid 0.85 g (3.3 millimole) and piperazine hexahydrate 10 g (50 millimole) was heated in a sealed tube at 125°–135° C. (inner temperature) for 22 hours. After cooling, the reaction mixture was evaporated under vacuum. The residue was acidified with acetic acid and the insoluble matters were removed by filtration. The filtrate was neutralized with an aqueous solution of caustic soda. The precipitated crystals were collected by filtration, washed with water and dried. The crystals were dissolved in hot diluted hydrochloric acid, reprecipitated with the addition of ethanol, collected by filtration and dried. Recrystallizing the crystals from a mixed solution of water and ethanol, 0.45 g (40%) of 1-methyl-6-fluoro-7-(1-piperazinyl)-4-oxo-1,4-dihydroquinoline-3-carboxylic acid hydrochloride was obtained. Colorless powders.

Melting point: not lower than 300° C.

Analysis: $C_{15}H_{16}O_3N_3F.HCl.\frac{1}{4} H_2O$

|  | C | H | N |
|---|---|---|---|
| Calculated (%) | 52.03 | 5.09 | 12.14 |
| Measured (%) | 52.23 | 4.99 | 12.03 |

EXAMPLE 19

The starting material for this example was prepared by the same method as in Example 5, using propyl bromide instead of 2-fluoroethyl iodide.

A mixture of 1-propyl-6-fluoro-7-chloro-4-oxo-1,4-dihydroquinoline-3-carboxylic acid 0.95 g (3.3 millimole) and piperazine hexahydrate 10 g (50 millimole) was heated in a sealed tube at 125°–135° C. (inner temperature) for 22 hours. After cooling, the reaction mixture was evaporated under vacuum, and the residue was acidified with acetic acid and the insoluble matters were removed by filtration. The filtrate was neutralized with an aqueous solution of caustic soda, extracted with the use of $CHCl_3$, washed with water, dried over anhydrous $Na_2SO_4$, and the solvent was evaporated off. The residue was dissolved in dilute hydrochloric acid, reprecipitated with the addition of ethanol. The precipitated crystals were collected by filtration, washed with ethanol and dried to obtain 0.2 g (16%) of 1-propyl-6-fluoro-7-(1-piperazinyl)-4-oxo-1,4-dihydroquinoline-3-carboxylic acid hydrochloride. Colorless powders.

Melting point: 293°–296° C. (decomposition).

Analysis: $C_{17}H_{20}O_{33}F.HCl.\frac{1}{2} H_2O$

|  | C | H | N |
|---|---|---|---|
| Calculated (%) | 54.55 | 5.79 | 11.23 |
| Measured (%) | 54.58 | 5.72 | 11.01 |

EXAMPLE 20

The starting material for this example was prepared by the same procedure as in Example 5, using benzyl chloride instead of 2-fluoroethyl iodide as an alkylating agent.

A mixture of 1-benzyl-6-fluoro-7-chloro-4-oxo-1,4-dihydroquinoline-3-carboxylic acid 1.1 g and piperazine hexahydrate 10 g was heated in a sealed tube at 125°–135° C. (inner temperature) for 22 hours. After cooling, the reaction mixture was evaporated under vacuum. The residue was dissolved in warm acetic acid and the insoluble matters was filtered off. The filtrate was neutralized with an aqueous solution of NaOH, and the precipitated crystals were collected by filtration, washed with water and dried. Recrystallizing the crystals from dimethylformamide, 1.0 g (79%) of 1-benzyl-6-fluoro-1,4-dihydro-4-oxo-7-(1-piperazinyl)-quinoline-3-carboxylic acid was obtained. Colorless powders.

Melting point: 250°–253° C.

Analysis: $C_{21}H_{20}O_3N_3F$

|  | C | H | N |
|---|---|---|---|
| Calculated (%) | 66.13 | 5.29 | 11.01 |
| Measured (%) | 66.02 | 5.18 | 10.95 |

EXAMPLE 21

The starting material for this example was prepared by the same method as in Example 5, using allyl bromide instead of 2-fluoroethyl iodide.

A mixture of 1-allyl-6-fluoro-7-chloro-1,4-dihydro-4-oxoquinoline-3-carboxylic acid 0.94 g, piperazine 2.9 g and 2 ml of pyridine was refluxed for 8 hours by heating. After cooling, the reaction mixture was evaporated under vacuum. The residue was dissolved in an aqueous solution of acetic acid and the insoluble matters were removed by filtration. The filtrate was neutralized with an aqueous solution of NaOH. The precipitated crystals were collected by filtration, washed with water and dried. Recrystallizing the crystals from a mixed solvent of concentrated hydrochloric acid and ethanol, 0.32 g (26%) of 1-allyl-6-fluoro-1,4-dihydro-4-oxo-(1-piperazinyl)-quinoline-3-carboxylic acid hydrochloride was obtained. Colorless powders.

Melting point: 290°–293° C. (decomposition).

Analysis: $C_{17}H_{18}O_3N_3F \cdot HCl$

|  | C | H | N |
|---|---|---|---|
| Calculated (%) | 55.51 | 5.21 | 11.42 |
| Measured (%) | 55.16 | 5.19 | 11.30 |

EXAMPLE 22

A mixture of 4-bromo-3-chloroaniline (8.3 g) and diethyl ethoxymethylene malonate (8.9 g) was heated at 120°–130° C. for 1.5 hours. The mixture was added to diphenyl ether (140 ml) and refluxed for 30 minutes. The cooled mixture was filtered, the solid was washed with benzene and dried. The solid was recrystallized from DMF to give 6-bromo-7-chloro-1,4-dihydro-4-oxoquinoline-3-carboxylic acid ethyl ester (11.7 g).

Melting point: above 300° C.

A mixture of the above ester (7.5 g), pottasium carbonate (7.8 g), ethyl iodide (9.0 ml) and DMF (100 ml was stirred at 90°–110° C. for 10 hours and evaporated. The residue was extracted with chloroform, the chloroform layer was washed with water, and dried. The solvent was evaporated. The residue was added to a solution of sodium hydroxide (4.2 g) and water (100 ml) and refluxed for 30 minutes. The alkaline solution was acidified with concentrated hydrochloric acid and the precipitate was filtered. The precipitate was washed with water, dried, and recrystallized from DMF to give 6-bromo-7-chloro-1-ethyl-1,4-dihydro-4-oxoquinoline-3-carboxylic acid (6.9 g).

Melting point: above 300° C.

A mixture of 1-ethyl-6-bromo-7-chloro-1,4-dihydro-4-oxoquinoline-3-carboxylic acid 1.65 g, piperazine 2.15 g and pyridine 2 ml was refluxed for 12 hours by heating. The reaction mixture was evaporated under vacuum and dissolved in aqueous acetic acid. The insoluble matters were removed by filtration. The filtrate was neutralized with an aqueous solution of NaOH. The precipitated crystals were collected by filtration and washed with water. The precipitate was recrystallized from a mixed solvent of concentrated hydrochloric acid and ethanol to obtain 1.4 g (67%) of 1-ethyl-6-bromo-dihydro-4-oxo-7-(1-piperazinyl)quinoline-3-carboxylic acid hydrochloride as colorless needles.

Melting point: above 300° C.

Analysis: $C_{16}H_{18}N_3O_3Br \cdot HCl$

|  | C | H | N |
|---|---|---|---|
| Calculated (%) | 46.12 | 4.60 | 10.08 |
| Measured (%) | 46.08 | 4.69 | 10.37 |

EXAMPLE 23

A mixture of 1-ethyl-6-bromo-7-chloro-1,4-dihydro-4-oxoquinoline-3-carboxylic acid 1.65 g, N-methylpiperazine 2.5 g and pyridine 2 ml was refluxed for 12 hours by heating. The reaction mixture was evaporated under vacuum. The residue was dissolved in an aqueous solution of acetic acid to separate insoluble matters by filtration and neutralized with an aqueous solution of NaOH. The precipitated crystals were collected by filtration and dried. Recrystallizing the precipitates from a mixed solvent of DMF and ethanol, 1.45 g (74%) of 1-ethyl-6-bromo-1,4-dihydro-7-(4-methyl-1-piperazinyl)-4-oxoquinoline-3-carboxylic acid was obtained as colorless needle crystals.

Melting point: 273°–275° C. (decomposition).

Analysis: $C_{17}H_{20}N_3O_3Br$

|  | C | H | N |
|---|---|---|---|
| Calculated (%) | 51.79 | 5.11 | 10.66 |
| Measured (%) | 51.70 | 5.16 | 10.92 |

EXAMPLE 24

3.2 g (10 millimole) of 1-ethyl-6-fluoro-7-(1-piperazinyl)-4-oxo-1,4-dihydroquinoline-3-carboxylic acid was dissolved in 30 ml of acetic acid, and 1.4 g (20 millimole) of sodium nitrite was added slowly thereto at room temperature under stirring. After stirring for 30 minutes at room temperature, 50 ml of water was added. The precipitated crystals were collected by filtration, washed successively with water, ethanol and dichloromethane and dried. 3.5 g (quantitative) of 1-ethyl-6-fluoro-7-(4-nitroso-1-piperazinyl)-4-oxo-1,4-dihydroquinoline-3-carboxylic acid was obtained as grayish colorless powders.

Melting point: 278°–280° C. (decomposition).

Analysis: $C_{16}H_{17}O_4N_4F \cdot \frac{1}{2} H_2O$

|  | C | H | N |
|---|---|---|---|
| Calculated (%) | 54.23 | 5.03 | 15.81 |
| Measured (%) | 54.30 | 4.88 | 15.58 |

EXAMPLE 25

The starting material of this example was prepared by the same method as in Example 5, using 2-bromoethanol instead of 2-fluoroethyl iodide.

A mixture of 1-(2-hydroxyethyl)-6-fluoro-7-chloro-4-oxo-1,4-dihydroquinoline-3-carboxylic acid 2.85 g (0.01 mole), piperazine 4.3 g (0.05 mole) and pyridine 4 ml was refluxed at 135°–145° C. for 8 hours by heating. After cooling, the reaction mixture was evaporated under vacuum. The residue was acidified with acetic acid and the insoluble matters were removed by filtration. The filtrate was neutralized with an aqueous solution of caustic soda. The precipitated crystals were collected by filtration, washed with water and dried. The crystals were dissolved in hot diluted hydrochloric acid, ethanol was added and the solution was cooled to precipitate crystals. The precipitated crystals were collected by filtration, washed with ethanol, dried, and recrystallized from ethanol to obtain 1.9 g (51%) of 1-(2-hydroxyethyl)-6-fluoro-7-(1-piperazinyl)-4-oxo-1,4-dihydroquinoline-3-carboxylic acid hydrochloride. Colorless powders.

Melting point: above 300° C.

Analysis: $C_{16}H_{18}O_4N_3F \cdot HCL \cdot \frac{1}{2} H_2O$

|  | C | H | N |
|---|---|---|---|
| Calculated (%) | 50.46 | 5.03 | 11.03 |
| Measured (%) | 50.21 | 5.18 | 10.68 |

EXAMPLE 26

A mixture of 1-(2-hydroxyethyl)-6-fluoro-7-(1-piperazinyl)-4-oxo-1,4-dihydroquinoline-3-carboxylic acid hydrochloride 1.50 g (4 millimole), anhydrous acetic acid 0.7 g (7 millimole), triethylamine 0.5 g (5 millimole) and DMF 5 ml was heated at 90°–100° C. for 3 hours under stirring. After cooling, the reaction mixture was evaporated under vacuum, and acidified with acetic acid. The precipitated crystals were collected by filtration, washed successively with water and ethanol and dried. 1.46 g (97%) of 1-(2-hydroxyethyl)-6-fluoro-7-(4-acetyl-1-piperazinyl)-4-oxo-1,4-dihydroquinoline-3-carboxylic acid was obtained as yellowish powders.

Melting point: 286°–290° C. (decomposition).
IR$\nu_{max}^{KBr}$ cm$^{-1}$: 1725 (COOH), 1625 (CO).
MS m/e: 377 (M+), 333 (M+—$CO_2$).

EXAMPLE 27

A mixture of 1-ethyl-1,4-dihydro-6-fluoro-4-oxo-(7-piperazinyl)quinoline-3-carboxylic acid 2.1 g, triethylamine 1.35 g, p-nitrobenzylbromide 2.2 g and dimethylformamide 50 ml was heated at 90° C. for 7 hours under stirring. The reaction solution was evaporated under vacuum, and water was added. The precipitated crystals were collected by filtration, washed with water and dried. The crystals were recrystallized from dimethylformamide to obtain 2.5 g (84%) of 1-ethyl-1,4-dihydro-6-fluoro-7-[4-(p-nitrobenzyl)-1-piperazinyl]-4-oxo-3-carboxylic acid as colorless powders.

Melting point: 230°–231° C.

Analysis: $C_{23}H_{23}O_5N_4F$

|  | C | H | N |
| --- | --- | --- | --- |
| Calculated (%) | 60.79 | 5.10 | 12.33 |
| Measured (%) | 60.96 | 5.30 | 12.43 |

EXAMPLE 28

A mixture of 1-ethyl-1,4-dihydro-6-fluoro-4-oxo-7-(1-piperazinyl)quinoline-3-carboxylic acid 0.5 g, 3-hydroxyphthalide 0.24 g and dimethylformamide 5 ml was heated at 100°–110° C. for 3 hours under stirring. After cooling, ethanol was added, and the insoluble matters were collected by filtration. The precipitates obtained were washed with ethanol and dried. 0.70 g (99%) of 1-ethyl-1,4-dihydro-6-fluoro-4-oxo-7-(4-phthalidyl-1-piperazinyl)quinoline-3-carboxylic acid was obtained as colorless powders.

Melting point: 285°–286° C. (decomposition).

Analysis: $C_{24}H_{22}N_3O_5F$

|  | C | H | N |
| --- | --- | --- | --- |
| Calculated (%) | 63.85 | 4.91 | 9.31 |
| Measured (%) | 63.90 | 4.86 | 9.19 |

EXAMPLE 29

1-ethyl-6-fluoro-1,4-dihydro-4-oxo-7-(1-piperazinyl)-quinoline-3-carboxylic acid 3.2 g was dissolved in 20 ml of glacial acetic acid, 2.0 g of anhydrous acetic acid was added thereto and the mixture was heated at 90°–100° C. for 2 hours with stirring. After cooling, 50 ml of water was added thereto. The precipitated crystals were collected by filtration, washed and dried. The crystals were recrystallized from dimethylformamide to obtain 3.5 g (97%) of 1-ethyl-6-fluoro-1,4-dihydro-4-oxo-7-(4-acetyl-1-piperazinyl)quinoline-3-carboxylic acid as colorless needles.

Melting point: 300° C.

Analysis: $C_{18}H_{20}N_3O_4F \cdot \frac{1}{4} H_2O$

|  | C | H | N |
| --- | --- | --- | --- |
| Calculated (%) | 59.09 | 5.65 | 11.49 |
| Measured (%) | 58.99 | 5.65 | 11.36 |

The antibacterial spectra of the present inventive compounds are shown in the following testing examples.

Testing Examples

The antibacterial tests were done according to the method authorized by the Chemotherapeutic Society of Japan. The results are shown in the following table.

| | | Antibacterial Spectrum (Minimum Inhibitory Concentration µg/ml) | | | | | | | | | |
| --- | --- | --- | --- | --- | --- | --- | --- | --- | --- | --- | --- |
| | | Compound (Example No.) | | | | | | | | | |
| Organisms tested | Gram | 1 | 2 | 3 | 4 | 5 | 6 | 7 | 8 | 9 | 10 |
| Bacillus subtilis PCI 219 | + | 0.39 | 0.10 | 0.39 | 0.39 | 0.20 | <0.10 | 0.20 | 0.78 | 0.78 | 0.78 |
| Staphylococcus aureus 209P | + | 0.78 | 0.39 | 3.13 | 1.56 | 1.56 | 0.39 | 0.39 | 3.13 | 1.56 | 0.78 |
| Sta. aureus ATCC 14775 | + | 6.25 | 0.39 | 6.25 | 3.13 | 6.25 | 0.78 | 0.39 | 6.25 | | |
| Mycobacterium smegmatis IFO 3083 | + | | | | | | | | | | |
| Escherichia coli NIHJ JC-2 | − | 0.20 | 0.10 | 0.10 | <0.10 | <0.10 | <0.10 | 0.39 | 0.39 | 1.56 | 1.56 |
| E. coli ATCC 10536 | − | 0.39 | 0.10 | 0.10 | 0.20 | 0.20 | 0.20 | 0.39 | 0.78 | 0.78 | 0.78 |
| Proteus vulgaris IFO 3167 | − | 0.20 | 0.20 | 0.20 | 0.20 | 0.20 | <0.10 | 0.78 | 0.78 | 0.78 | 1.56 |
| Pr. vulgaris XK Denken | − | 0.39 | 0.20 | 0.39 | 0.20 | 0.39 | <0.10 | 0.78 | 0.39 | 0.78 | 1.56 |
| Klebsiella pneumoniae IFO 3512 | − | 0.20 | <0.025 | 0.10 | <0.10 | <0.10 | <0.10 | 0.10 | 0.10 | <0.20 | <0.20 |
| Salmonella enteritidies IID 604 | − | 0.39 | | | 0.78 | 0.78 | 0.78 | 3.13 | 12.5 | | |
| Shigella sonnei IID 969 | − | | | | 0.20 | <0.10 | <0.10 | | | | |
| Pseudomonas aeruginosa V-1 | − | 3.13 | 3.13 | 0.39 | 3.13 | 0.78 | 3.13 | 12.5 | 12.5 | 25 | 50 |
| Ps. aeruginosa IFO 12689 | − | 6.25 | 6.25 | 1.56 | 3.13 | 3.13 | 3.13 | 25 | 25 | 50 | >100 |
| Ps. aeruginosa IID 1210 | − | 6.25 | | 1.56 | 3.13 | 3.13 | 6.25 | 25 | >25 | | |
| Ps. aeruginosa IID 1130 | − | 1.56 | | 1.56 | 6.25 | 1.56 | 6.25 | 25 | 25 | | |
| Serratia marcescens IID 618 | − | 0.39 | 0.39 | | 0.39 | 0.20 | 0.20 | 3.13 | 6.25 | | |
| Ser. marcescens IID 619 | − | 0.78 | 0.39 | | 0.78 | 0.39 | 0.20 | 3.13 | 12.5 | | |
| Ser. marcescens IID 620 | − | 0.39 | 0.39 | | 0.39 | 0.20 | 0.20 | | 6.25 | | |

| | | Compound (Example No.) | | | | | | | | | | |
| --- | --- | --- | --- | --- | --- | --- | --- | --- | --- | --- | --- | --- |
| Organisms tested | Gram | 11 | 12 | 13 | 14 | 15 | 16 | 17 | 18 | 19 | 20 | 21 | 22 |
| Bacillus subtilis PCI 219 | + | 1.56 | 0.78 | 3.13 | 50 | 0.78 | 3.13 | 50 | 0.78 | 0.39 | 0.78 | 0.78 | 1.56 |
| Staphylococcus aureus 209P | + | 3.13 | 1.56 | >100 | 50 | 1.56 | 12.5 | 50 | 6.25 | 1.56 | 1.56 | 3.13 | 3.13 |

Antibacterial Spectrum (Minimum Inhibitory Concentration μg/ml) -continued

| Organism | Gram | | | | | | | | | | | | |
|---|---|---|---|---|---|---|---|---|---|---|---|---|---|
| Sta. aureus ATCC 14775 | + | | | | | 25 | 100 | 12.5 | 3.13 | 6.25 | 6.25 | 12.5 | |
| Mycobacterium smegmatis IFO 3083 | + | | | 25 | >100 | | | | | | | | |
| Escherichia coli NIHJ JC-2 | − | 100 | 3.13 | 100 | 12.5 | 0.20 | 0.78 | 12.5 | 0.39 | 0.20 | 0.78 | 0.20 | 0.39 |
| E. coli ATCC 10536 | − | 25 | 0.78 | 100 | 12.5 | 0.20 | 0.78 | 6.25 | 0.39 | 0.39 | 0.39 | 0.20 | 0.78 |
| Proteus vulgaris IFO 3167 | − | 100 | 0.78 | 100 | 25 | 0.39 | 0.78 | 12.5 | 0.39 | 0.20 | 0.39 | 0.20 | 0.39 |
| Pr. vulgaris XK Denken | − | 50 | 0.78 | 50 | 12.5 | 0.39 | 1.56 | 25 | 1.56 | 0.39 | 0.78 | 0.39 | 1.56 |
| Klebsiella pneumoniae IFO 3512 | − | 0.78 | 0.78 | 6.25 | 12.5 | 0.78 | 0.20 | 6.25 | 0.39 | 0.20 | 0.39 | 0.20 | 0.39 |
| Salmonella enteritidies IID 604 | − | | | | | | | | | | | | 1.56 |
| Shigella sonnei IID 969 | − | | | | | | | | | | | | 0.39 |
| Pseudomonas aeruginosa V-1 | − | >100 | 25 | >100 | >100 | 6.25 | 1.56 | 50 | 1.56 | 3.13 | 1.56 | 1.56 | 12.5 |
| Ps. aeruginosa IFO 12689 | − | >100 | 50 | >100 | >100 | 12.5 | 12.5 | >100 | 3.13 | 12.5 | 6.25 | 6.25 | 50 |
| Ps. aeruginosa IID 1210 | − | | | | | | | | | | | | 100 |
| Ps. aeruginosa IID 1130 | − | | | | | | | | | | | | 50 |
| Serratia marcescens IID 618 | − | | | | | | | | | | | | 0.78 |
| Ser. marcescens IID 619 | − | | | | | | | | | | | | 3.13 |
| Ser. marcescens IID 620 | − | | | | | | | | | | | | 0.78 |

| Organisms tested | Gram | Compound (Example No.) | | | | | | | Comparison | |
|---|---|---|---|---|---|---|---|---|---|---|
| | | 23 | 24 | 25 | 26 | 27 | 28 | 29 | Nalidixic acid | Pipemidic acid |
| Bacillus subtilis PCI 219 | + | 0.78 | 0.39 | 1.56 | 12.5 | 0.10 | 0.20 | 0.20 | 6.25 | 6.25 |
| Staphylococcus aureus 209P | + | 1.56 | 0.39 | 1.56 | >25 | 1.56 | 0.78 | 0.78 | 100 | 25 |
| Sta. aureus ATCC 14775 | + | 3.13 | 0.78 | >25 | >25 | 3.13 | 3.13 | 1.56 | >100 | 100 |
| Mycobacterium smegmatis IFO 3083 | + | | | | | | | | >100 | 50 |
| Escherichia coli NIHJ JC-2 | − | 0.39 | 0.39 | 0.39 | >25 | 6.25 | ≦0.05 | 1.56 | 3.13 | 1.56 |
| E. coli ATCC 10536 | − | 0.78 | 0.39 | 0.20 | 25 | 6.25 | 0.10 | 1.56 | 3.13 | 1.56 |
| Proteus vulgaris IFO 3167 | − | 0.78 | 0.39 | 0.20 | >25 | 6.25 | ≦0.05 | 0.39 | 3.13 | 3.13 |
| Pr. vulgaris XK Denken | − | 3.13 | 0.39 | 3.13 | >25 | 12.5 | 0.20 | 1.56 | 3.13 | 6.25 |
| Klebsiella pneumoniae IFO 3512 | − | 0.39 | 0.39 | 0.05 | 6.25 | 0.10 | ≦0.05 | <0.10 | 1.56 | 1.56 |
| Salmonella enteritidies IID 604 | − | 3.13 | | | | | 0.10 | | 12.5 | 12.5 |
| Shigella sonnei IID 969 | − | 0.78 | | | | 6.25 | | | 1.56 | 1.56 |
| Pseudomonas aeruginosa V-1 | − | 100 | 3.13 | 3.13 | >25 | >50 | 0.78 | 25 | 100 | 12.5 |
| Ps. aeruginosa IFO 12689 | − | >100 | 6.25 | >25 | >25 | >50 | 1.56 | 25 | >200 | 25 |
| Ps. aeruginosa IID 1210 | − | >100 | | | | | 1.56 | | >200 | 50 |
| Ps. aeruginosa IID 1130 | − | >100 | | | | | 1.56 | | >200 | 25 |
| Serratia marcescens IID 618 | − | 0.78 | | | | | 0.10 | | | |
| Ser. marcescens IID 619 | − | 3.13 | | | | | 0.20 | | | |
| Ser. marcescens IID 620 | − | 0.78 | | | | | 0.10 | | | |

We claim:

1. 1-Ethyl-1,4-dihydro-6-fluoro-7-(1-piperazinyl)-4-oxo-1,8-naphthyridine-3-carboxylic acid, the pharmacologically acceptable hydrates and acid addition salts thereof.

2. 1-Ethyl-1,4-dihydro-6-fluoro-7-(1-piperazinyl)-4-oxo-1,8-naphthyridine-3-carboxylic acid hydrochloride.

3. 1-Ethyl-7-(4-p-aminobenzyl-1-piperazinyl)-1,4-dihydro-6-fluoro-4-oxo-quinoline-3-carboxylic acid.

* * * * *

Disclaimer 4,448,962.—*Tsutomu Irikura*, Tokyo; *Seigo Suzue*, Saitama; *Akira Ito*, Saitama; *Hiroshi Koga*, Saitama, all of Japan. SUBSTITUTED QUINOLINE CARBOXYLIC ACID DERIVATIVES. Patent dated May 15, 1984. Disclaimer filed Sept. 23, 1985, by the assignee, *Kyorin Seiyaku Kabushiki Kaisha.*

Hereby enters this disclaimer to all claims of said patent.

[*Official Gazette November 19, 1985.*]